United States Patent [19]
Gerlach et al.

[11] Patent Number: 6,087,399
[45] Date of Patent: Jul. 11, 2000

[54] SULFONAMIDE-SUBSTITUTED COMPOUNDS, PROCESS FOR THEIR PREPARATION, THEIR USE AS A MEDICAMENT OR DIAGNOSTIC, AND A MEDICAMENT COMPRISING THEM

[75] Inventors: Uwe Gerlach, Hattersheim; Joachim Brendel, Bad Vilbel; Hans Jochen Lang, Hofheim; Klaus Weidmann, Kronberg, all of Germany

[73] Assignee: Hoechst Aktiengesellschaft, Frankfurt am Main, Germany

[21] Appl. No.: 09/299,726

[22] Filed: Apr. 27, 1999

Related U.S. Application Data

[63] Continuation of application No. 09/021,130, Feb. 10, 1998, abandoned.

[30] Foreign Application Priority Data

Feb. 11, 1997 [DE] Germany ............... 197 05 133

[51] Int. Cl.[7] ............... C07D 211/62; A61K 31/18; C07C 311/08
[52] U.S. Cl. ............... 514/605; 564/99
[58] Field of Search ............... 564/99; 514/605

[56] References Cited

FOREIGN PATENT DOCUMENTS

| 0 386 839 A3 | 3/1990 | European Pat. Off. . |
| 0 807 629 A1 | 11/1997 | European Pat. Off. . |
| 57-183751 | 11/1982 | Japan . |
| WO 95/14669 | 6/1995 | WIPO . |

OTHER PUBLICATIONS

Paul D. Leeson et al., "4–Amido–2–carboxytetrahydroquinolines. Structure–Activity Relationships for Antagonism at the Glycine Site of the NMDA Receptor," *J. Med. Chem*, vol. 35, pp. 1954–1968 (1992).

Thomas J. Colatsky et al., "Channel Specificity in Antiarrhythmic Drug Action: Mechanism of Potassium Channel Block and Its Role in Suppressing and Aggravating Cardiac Arrhythmias," *Circulation*, vol. 82, No. 6, pp. 2235–2242 (Dec. 1990).

Andreas E. Busch et al., "The Novel Class III Antiarrhythmics NE–10064 and NE–10133 Inhibit $I_{SK}$ Channels Expressed in Xenopus Oocytes and $I_{KS}$ in Guinea Pig Cardiac Myoctyes," *Biochemical and Biophysical Research Communications*, vol. 202, No. 1, pp. 265–270 (Jul. 15, 1994).

*Primary Examiner*—Zinna Northington Davis
*Attorney, Agent, or Firm*—Finnegan, Henderson, Farabow, Garrett & Dunner, L.L.P.

[57] ABSTRACT

Compounds of formula I

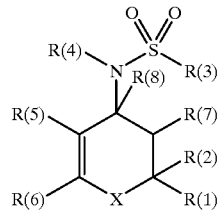

in which R(1) to R(8) and X have the meanings indicated in the specification, are useful for the production of medicaments having $K^+$ channel-blocking action; in particular for the production of a medicament for the treatment or prophylaxis of stimulated gastric acid secretion; of ulcers of the stomach and of the intestinal region; of reflux esophagitis; of diarrhea; of all types of arrhythmias, including ventricular and supraventricular arrhythmias; and of reentry arrhythmias and for the prophylaxis of sudden heart death as a result of ventricular fibrillation.

17 Claims, No Drawings

SULFONAMIDE-SUBSTITUTED COMPOUNDS, PROCESS FOR THEIR PREPARATION, THEIR USE AS A MEDICAMENT OR DIAGNOSTIC, AND A MEDICAMENT COMPRISING THEM

This is a continuation of application Ser. No. 09/021,130, filed Feb. 10, 1998, now abandoned based on German Patent Application No. 19705133.2, filed Feb. 11, 1997 now abandoned, all of which are incorporated herein by reference.

FIELD OF THE INVENTION

The compounds are distinguished as a novel active compound class of potent inhibitors of stimulated gastric acid secretion. The compounds of formula I are thus useful medicaments for the treatment of ulcers of the stomach and of the intestinal region, for example of the duodenum. As a result of their strong gastric secretion-inhibiting action, they are likewise suitable as excellent therapeutics for the treatment of reflux esophagitis.

BACKGROUND OF THE INVENTION

The invention relates to compounds of formula I

I in which:

X is $—S(O)_{zero,\ 1\ or\ 2}—$, $—NR(9)—$, $—CR(9)R(23)—$ or $—CO—$;

R(9) is hydrogen or $—(C_nH_{2n})—R(10)$;
  n is zero, 1, 2, 3, 4, 5, 6, 7 or 8;
  R(10) is hydrogen, cycloalkyl having 3, 4, 5, 6, 7 or 8 carbon atoms, piperidyl, 1-pyrrolidinyl, N-morpholino, N-methylpiperazino, $CF_3$, $C_2F_5$ or $C_3F_7$;
    where a $CH_2$-group of the group $C_nH_{2n}$ can be replaced by $—O—$, $—CH=CH—$, $—C\equiv C—$, $—CO—$, $—CO—O—$, $—SO_{zero,\ 1\ or\ 2}—$ or $—NR(11)—$;
  R(11) is hydrogen, methyl or ethyl;
  or
  R(10) is pyridyl, thienyl, imidazolyl or phenyl,
    each of which is unsubstituted or substituted by 1 or 2 substituents selected from the group consisting of F, Cl, Br, I, $CF_3$, methyl, methoxy, sulfamoyl, methylsulfonyl and methylsulfonylamino;
  or
  R(9) together with R(1) is a bond;
R(23) is hydrogen, alkyl having 1, 2 or 3 carbon atoms, OH, O-alkyl having 1, 2 or 3 carbon atoms, COOH, COO-alkyl having 1, 2 or 3 carbon atoms or $—CO—R(24)$;
  R(24) is hydrogen, methyl or ethyl;
R(1) and R(2)
  independently of one another are hydrogen, $CF_3$, $C_2F_5$, $C_3F_7$, alkyl having 1, 2, 3, 4, 5 or 6 carbon atoms or phenyl,
    each of which is unsubstituted or substituted by 1 or 2 substituents selected from the group consisting of F, Cl, Br, I, $CF_3$, methyl, methoxy, sulfamoyl and methylsulfonyl;
  or
R(1) and R(2)
  together are an alkylene chain having 2, 3, 4, 5, 6, 7, 8, 9 or 10 carbon atoms;
R(3) is $R(12)—C_aH_{2a}NR(13)_m—$;
  R(12) is hydrogen or cycloalkyl having 3, 4, 5, 6, 7 or 8 carbon atoms, $CF_3$, $C_2F_5$ or $C_3F_7$;
  a is zero, 1, 2, 3, 4, 5, 6, 7, 8, 9 or 10;
  m is zero or 1;
  R(13) is hydrogen or alkyl having 1, 2, 3, 4, 5 or 6 carbon atoms;
  or
  R(12) and R(13)
    together are an alkylene group having 4, 5, 6, 7 or 8 carbon atoms,
      where a $CH_2$ group of the alkylene group can be replaced by $—O—$, $—SO_{zero,\ 1\ or\ 2}—$, $—CO—$ or $—NR(11)—$;
    R(11) is hydrogen, methyl or ethyl;
R(4) is $R(14)—C_rH_{2r}$;
  r is 1, 2, 3, 4, 5, 6, 7, 8, 9, 10, 11, 12, 13, 14, 15, 16, 17, 18, 19 or 20;
  R(14) is hydrogen, cycloalkyl having 3, 4, 5, 6, 7 or 8 carbon atoms, piperidyl, 1-pyrrolidinyl, N-morpholino, N-methylpiperazino, $CF_3$, $C_2F_5$, $C_3F_7$, pyridyl, thienyl, imidazolyl or phenyl,
    each of which is unsubstituted or substituted by 1 or 2 substituents selected from the group consisting of F, Cl, Br, I, $CF_3$, methyl, methoxy, sulfamoyl, methylsulfonyl and methylsulfonylamino;
  where a $CH_2$ group of the group $C_rH_{2r}$ can be replaced by $—O—$, $—CH=CH—$, $—C\equiv C—$, $—CO—$, $—CO—O—$, $—CO—NR(11)—$, $—SO_{zero,\ 1\ or\ 2}—$ or $—NR(11)—$;
or
R(3) and R(4)
  together are an alkylene chain having 3, 4, 5, 6, 7 or 8 carbon atoms,
    where a $CH_2$ group of the alkylene chain can be replaced by $—O—$, $—SO_{zero\ 1\ or\ 2}—$, $—CO—$ or $—NR(11)—$;
R(5) and R(6)
  together are $—CR(15)=CR(16)—CR(17)=CR(18)—$, $—CR(15)=CR(16)—CR(17)=N—$, $—CR(15)=CR(16)—N=CR(18)—$, $—CR(15)=N—CR(17)=N—$, $—CR(15)=N—N=CR(18)—$, $—N=CR(16)—CR(17)=N—$ or $—S—CR(15)=CR(16)—$;
  R(15), R(16), R(17) and R(18)
    independently of one another are hydrogen, F, Cl, Br, I, alkyl having 1, 2, 3 or 4 carbon atoms, cycloalkyl having 3, 4, 5, 6, 7 or 8 carbon atoms, CN, $CF_3$, $C_2F_5$, $C_3F_7$, $N_3$, $NO_2$, $—CONR(19)R(20)$, $—COOR(21)$, $R(22)—C_sH_{2s}—Z—$ or phenyl,
      each of which is unsubstituted or substituted by 1 or 2 substituents selected from the group consisting of F, Cl, Br, I, $CF_3$, methyl, methoxy, sulfamoyl and methylsulfonyl;
  R(19) and R(20) independently of one another are hydrogen or alkyl having 1, 2 or 3 carbon atoms;
  R(21) is hydrogen, methyl, ethyl, phenyl or $—C_uH_{2u}—NR(19)R(20)$;

u is 2 or 3;
where the phenyl is unsubstituted or substituted by 1 or 2 substituents selected from the group consisting of F, Cl, Br, I, $CF_3$, methyl, methoxy, sulfamoyl or methylsulfonyl;

R(22) is hydrogen, cycloalkyl having 3, 4, 5, 6, 7 or 8 carbon atoms, —COOR(21), thienyl, imidazolyl, pyridyl, quinolyl, isoquinolyl, piperidyl, 1-pyrrolidinyl, N-morpholino, N-methylpiperazino, $CF_3$, $C_2F_5$ or $C_3F_7$ or phenyl,
each of which is unsubstituted or substituted by 1 or 2 substituents selected from the group consisting of F, Cl, Br, I, $CF_3$, methyl, methoxy, sulfamoyl or methylsulfonyl;

s is zero, 1, 2, 3, 4, 5 or 6;

Z is —$S(O)_{zero,\ 1\ or\ 2}$—, —CO—, —$SO_2$—NR(11)—, —$SO_2$—O—, —O—, —NR(11)— or —CO—NR(11)—;

R(7) is hydrogen, hydroxyl, alkoxy having 1, 2, 3 or 4 carbon atoms, acyloxy having 1, 2, 3 or 4 carbon atoms, Cl, Br, F, alkyl having 1, 2, 3 or 4 carbon atoms;

R(8) is hydrogen or alkyl having 1, 2, 3, 4, 5 or 6 carbon atoms;

or physiologically tolerable salts thereof.

Preferred compounds of formula I are those in which:

X is —$S(O)_{zero,\ 1\ or\ 2}$—, —NR(9)— or —CR(9)R(23)—;

R(9) is hydrogen or —$(C_nH_{2n})$—R(10);

n is zero, 1, 2, 3, 4, 5, 6, 7 or 8;

R(10) is hydrogen, cycloalkyl having 3, 4, 5, 6, 7 or 8 carbon atoms, piperidyl, 1-pyrrolidinyl, N-morpholino, N-methylpiperazino, $CF_3$, $C_2F_5$ or $C_3F_7$;
where a $CH_2$ group of the group $C_nH_{2n}$ can be replaced by —O—, —CH=CH—, —C≡C—, —CO—, —CO—O—, —$SO_{zero,\ 1\ or\ 2}$— or —NR(11)—;

R(11) is hydrogen, methyl or ethyl;

or

R(10) is pyridyl, thienyl, imidazolyl or phenyl,
each of which is unsubstituted or substituted by 1 or 2 substituents selected from the group consisting of F, Cl, Br, I, $CF_3$, methyl, methoxy, sulfamoyl, methylsulfonyl and methylsulfonylamino;

or

R(9) together with R(1) is a bond;

R(23) is hydrogen, alkyl having 1, 2 or 3 carbon atoms, OH, O-alkyl having 1, 2 or 3 carbon atoms, COOH, COO-alkyl having 1, 2 or 3 carbon atoms or —CO—R(24);

R(24) is hydrogen, methyl or ethyl;

R(1) and R(2)
independently of one another are hydrogen, $CF_3$, $C_2F_5$, $C_3F_7$, alkyl having 1, 2, 3, 4, 5 or 6 carbon atoms or phenyl,
each of which is unsubstituted or substituted by 1 or 2 substituents selected from the group consisting of F, Cl, Br, I, $CF_3$, methyl, methoxy, sulfamoyl and methylsulfonyl;

or

R(1) and R(2)
together are an alkylene chain having 2, 3, 4, 5, 6, 7, 8, 9 or 10 carbon atoms;

R(3) is R(12)—$C_aH_{2a}(NR(13))_m$—;

R(12) is hydrogen or cycloalkyl having 3, 4, 5, 6, 7 or 8 carbon atoms, $CF_3$, $C_2F_5$ or $C_3F_7$;

a is zero, 1, 2, 3, 4, 5, 6, 7, 8, 9 or 10;

m is zero or 1;

R(13) is hydrogen or alkyl having 1, 2, 3, 4, 5 or 6 carbon atoms;

or

R(12) and R(13)
together are an alkylene group having 4, 5, 6, 7 or 8 carbon atoms,
where a $CH_2$ group of the alkylene group can be replaced by —O—, —$SO_{zero,\ 1\ or\ 2}$—, —CO— or —NR(11)—;

R(11) is hydrogen, methyl or ethyl;

R(4) is R(14)—$C_rH_{2r}$;

r is 1, 2, 3, 4, 5, 6, 7, 8, 9, 10, 11, 12, 13, 14, 15, 16, 17, 18, 19 or 20;

R(14) is hydrogen, cycloalkyl having 3, 4, 5, 6, 7 or 8 carbon atoms, piperidyl, 1-pyrrolidinyl, N-morpholino, N-methylpiperazino, $CF_3$, $C_2F_5$, $C_3F_7$, pyridyl, thienyl, imidazolyl or phenyl,
each of which is unsubstituted or substituted by 1 or 2 substituents selected from the group consisting of F, Cl, Br, I, $CF_3$, methyl, methoxy, sulfamoyl, methylsulfonyl and methylsulfonylamino;
where a $CH_2$ group of the group $C_rH_{2r}$ can be replaced by —O—, —CH=CH—, —C≡C—, —CO—, —CO—O—, —CO—NR(11)—, $SO_{zero,\ 1\ or\ 2}$— or —NR(11)—;

or

R(3) and R(4)
together are an alkylene chain having 3, 4, 5, 6, 7 or 8 carbon atoms,
where a $CH_2$ group of the alkylene chain can be replaced by —O—, —$SO_{zero,\ 1\ or\ 2}$—, —CO— or —NR(11)—;

R(5) and R(6)
together are —CR(15)=CR(16)—CR(17)=CR(18)— or —S—CR(15)=CR(16)—;

R(15), R(16), R(17) and R(18)
independently of one another are hydrogen, F, Cl, Br, I, alkyl having 1, 2, 3 or 4 carbon atoms, cycloalkyl having 3, 4, 5, 6, 7 or 8 carbon atoms, CN, $CF_3$, $C_2F_5$, $C_3F_7$, $N_3$, $NO_2$, —CONR(19)R(20), —COOR(21), R(22)—$C_sH_{2s}$—Z— or phenyl,
each of which is unsubstituted or substituted by 1 or 2 substituents selected from the group consisting of F, Cl, Br, I, $CF_3$, methyl, methoxy, sulfamoyl and methylsulfonyl;

R(19) and R(20)
independently of one another are hydrogen or alkyl having 1, 2 or 3 carbon atoms;

R(21) is hydrogen, methyl, ethyl, phenyl or —$C_uH_{2u}$—NR(19)R(20);

u is 2 or 3;
where the phenyl is unsubstituted or substituted by 1 or 2 substituents selected from the group consisting of F, Cl, Br, I, $CF_3$, methyl, methoxy, sulfamoyl or methylsulfonyl;

R(22) is hydrogen, cycloalkyl having 3, 4, 5, 6, 7 or 8 carbon atoms, —COOR(21), thienyl, imidazolyl, pyridyl, quinolyl, isoquinolyl, piperidyl, 1-pyrrolidinyl, N-morpholino, N-methylpiperazino, $CF_3$, $C_2F_5$ or $C_3F_7$ or phenyl,
each of which is unsubstituted or substituted by 1 or 2 substituents selected from the group consisting of F, Cl, Br, I, $CF_3$, methyl, methoxy, sulfamoyl or methylsulfonyl;

s is zero, 1, 2, 3, 4, 5 or 6;

Z is $-S(O)_{zero,\ 1\ or\ 2}-$, $-CO-$, $SO_2-NR(11)-$, $-SO_2-O-$, $-O-$, $-NR(11)-$ or $-CO-NR(11)-$;

R(7) is hydrogen, hydroxyl, alkoxy having 1, 2, 3 or 4 carbon atoms, acyloxy having 1, 2, 3 or 4 carbon atoms, Cl, Br, F, alkyl having 1, 2, 3 or 4 carbon atoms;

R(8) is hydrogen or alkyl having 1, 2, 3, 4, 5 or 6 carbon atoms.

or physiologically tolerable salts thereof.

Particularly preferred compounds of formula 1 are those in which:

X is $-NR(9)-$ or $-CR(9)R(23)-$;
  R(9) is hydrogen or $-(C_nH_{2n})-R(10)$;
    n is zero, 1, 2, 3, 4, 5, 6, 7 or 8;
      R(10) is hydrogen, cycloalkyl having 3, 4, 5, 6, 7 or 8 carbon atoms, piperidyl, 1-pyrrolidinyl, N-morpholino, N-methylpiperazino, $CF_3$, $C_2F_5$ or $C_3F_7$;
      where a $CH_2$ group of the group $C_nH_{2n}$ can be replaced by $-O-$, $-CH=CH-$, $-C\equiv C-$, $-CO-$, $-CO-O-$, $-SO_{zero,\ 1\ or\ 2}-$ or $-NR(11)-$;
      R(11) is hydrogen, methyl or ethyl;
    or
    R(10) is pyridyl, thienyl, imidazolyl or phenyl,
      each of which is unsubstituted or substituted by 1 or 2 substituents selected from the group consisting of F, Cl, Br, I, $CF_3$, methyl, methoxy, sulfamoyl, methylsulfonyl and methylsulfonylamino;
  or
  R(9) together with R(1) is a bond;
  R(23) is hydrogen, alkyl having 1, 2 or 3 carbon atoms, OH, O-alkyl having 1, 2 or 3 carbon atoms, COOH, COO-alkyl having 1, 2 or 3 carbon atoms or $-CO-R(24)$;
  R(24) is hydrogen, methyl or ethyl;

R(1) and R(2)
  independently of one another are hydrogen, $CF_3$, $C_2F_5$, $C_3F_7$, alkyl having 1, 2, 3, 4, 5 or 6 carbon atoms or phenyl,
    each of which is unsubstituted or substituted by 1 or 2 substituents selected from the group consisting of F, Cl, Br, I, $CF_3$, methyl, methoxy, sulfamoyl and methylsulfonyl;
or
R(1) and R(2)
  together are an alkylene chain having 2, 3, 4, 5, 6, 7, 8, 9 or 10 carbon atoms;

R(3) is $R(12)-C_aH_{2a}(NR(13))_m-$;
  R(12) is hydrogen or cycloalkyl having 3, 4, 5, 6, 7 or 8 carbon atoms, $CF_3$, $C_2F_5$ or $C_3F_7$;
  a is zero, 1, 2, 3, 4, 5, 6, 7, 8, 9 or 10;
  m is zero or 1;
  R(13) is hydrogen or alkyl having 1, 2, 3, 4, 5 or 6 carbon atoms;
or
  R(12) and R(13)
    together are an alkylene group having 4, 5, 6, 7 or 8 carbon atoms,
      where a $CH_2$ group of the alkylene group can be replaced by $-O-$, $-(SO_{zero,\ 1\ or\ 2})-$, $-CO-$ or $-NR(11)-$;
      R(11) is hydrogen, methyl or ethyl;

R(4) is $R(14)-C_rH_{2r}$;

r is 1, 2, 3, 4, 5, 6, 7, 8, 9 or 10;
R(14) is hydrogen, cycloalkyl having 3, 4, 5, 6, 7 or 8 carbon atoms, piperidyl, 1-pyrrolidinyl, N-morpholino, N-methylpiperazino, $CF_3$, $C_2F_5$, $C_3F_7$, pyridyl, thienyl, imidazolyl or phenyl,
  each of which is unsubstituted or substituted by 1 or 2 substituents selected from the group consisting of F, Cl, Br, I, $CF_3$, methyl, methoxy, sulfamoyl, methylsulfonyl and methylsulfonylamino;
  where a $CH_2$ group of the group $C_rH_{2r}$ can be replaced by $-O-$, $-CH=CH-$, $-C\equiv C-$, $-CO-$, $-CO-O-$, $-CO-NR(11)-$, $-(SO_{zero,\ 1\ or\ 2})-$ or $-NR(11)-$;

or

R(3) and R(4)
  together are an alkylene chain having 3, 4, 5, 6, 7 or 8 carbon atoms,
    where a $CH_2$ group of the alkylene chain can be replaced by $-O-$, $-(SO_{zero,\ 1\ or\ 2})-$, $-CO-$ or $-NR(11)-$;

R(5) and R(6)
  together are $-CR(15)=CR(16)-CR(17)=CR(18)-$;

R(15), R(16), R(17) and R(18)
  independently of one another are hydrogen, F, Cl, Br, I, alkyl having 1, 2, 3 or 4 carbon atoms, cycloalkyl having 3, 4, 5, 6, 7 or 8 carbon atoms, CN, $CF_3$, $C_2F_5$, $C_3F_7$, $N_3$, $NO_2$, $-CONR(19)R(20)$, $-COOR(21)$, $R(22)-C_sH_{2s}-Z-$ or phenyl,
    each of which is unsubstituted or substituted by 1 or 2 substituents selected from the group consisting of F, Cl, Br, I, $CF_3$, methyl, methoxy, sulfamoyl and methylsulfonyl;

R(19) and R(20)
  independently of one another are hydrogen or alkyl having 1, 2 or 3 carbon atoms;

R(21) is hydrogen, methyl, ethyl, phenyl or $-C_uH_{2u}-NR(19)R(20)$;
  u is 2 or 3;
    where the phenyl is unsubstituted or substituted by 1 or 2 substituents selected from the group consisting of F, Cl, Br, I, $CF_3$, methyl, methoxy, sulfamoyl or methylsulfonyl;

R(22) is hydrogen, cycloalkyl having 3, 4, 5, 6, 7 or 8 carbon atoms, $-COOR(21)$, thienyl, imidazolyl, pyridyl, quinolyl, isoquinolyl, piperidyl, 1-pyrrolidinyl, N-morpholino, N-methylpiperazino, $CF_3$, $C_2F_5$ or $C_3F_7$ or phenyl,
  each of which is unsubstituted or substituted by 1 or 2 substituents selected from the group consisting of F, Cl, Br, I, $CF_3$, methyl, methoxy, sulfamoyl or methylsulfonyl;

s is zero, 1, 2, 3, 4, 5 or 6;

Z is $-S(O)_{zero,\ 1\ or\ 2}-$, $-CO-$, $-SO_2-NR(11)-$, $-SO_2-O-$, $-O-$, $-NR(11)-$ or $-CO-NR(11)-$;

R(7) is hydrogen, hydroxyl, alkoxy having 1, 2, 3 or 4 carbon atoms, acyloxy having 1, 2, 3 or 4 carbon atoms, Cl, Br, F, alkyl having 1, 2, 3 or 4 carbon atoms;

R(8) is hydrogen or alkyl having 1, 2, 3, 4, 5 or 6 carbon atoms;

or physiologically tolerable salts thereof.

When R(9) together with R(1) is a bond, this results in a second double bond in the six membered ring.

Very particularly preferred compounds of formula I are those in which:

X is —NR(9)— or —CR(9)R(23)—;
  R(9) is hydrogen or —($C_nH_{2n}$)—R(10);
    n is zero, 1, 2, 3, 4, 5, 6, 7 or 8;
    R(10) is hydrogen, cycloalkyl having 3, 4, 5, 6, 7 or 8 carbon atoms, piperidyl, 1-pyrrolidinyl, N-morpholino, N-methylpiperazino, $CF_3$, $C_2F_5$ or $C_3F_7$;
      where a $CH_2$ group of the group $C_nH_{2n}$ can be replaced by —O—, —CH=CH—, —C≡C—, —CO—, CO—O—, —$SO_{zero,\ 1\ or\ 2}$— or —NR(11)—;
    R(11) is hydrogen, methyl or ethyl;
    or
    R(10) is pyridyl, thienyl, imidazolyl or phenyl,
      each of which is unsubstituted or substituted by 1 or 2 substituents selected from the group consisting of F, Cl, Br, I, $CF_3$, methyl, methoxy, sulfamoyl, methylsulfonyl and methylsulfonylamino;
  R(23) is hydrogen, alkyl having 1, 2 or 3 carbon atoms, OH, O-alkyl having 1, 2 or 3 carbon atoms, COOH, COO-alkyl having 1, 2 or 3 carbon atoms or —CO—R(24);
R(1) and R(2)
  independently of one another are hydrogen, $CF_3$, $C_2F_5$, $C_3F_7$, alkyl having 1, 2, 3, 4, 5 or 6 carbon atoms or phenyl,
    each of which is unsubstituted or substituted by 1 or 2 substituents selected from the group consisting of F, Cl, Br, I, $CF_3$, methyl, methoxy, sulfamoyl and methylsulfonyl;
or
R(1) and R(2)
  together are an alkylene chain having 2, 3, 4, 5, 6, 7, 8, 9 or 10 carbon atoms;
R(3) is R(12)—$C_aH_{2a}$(NR(13))$_m$—;
  R(12) is hydrogen or cycloalkyl having 3, 4, 5, 6, 7 or 8 carbon atoms, $CF_3$, $C_2F_5$ or $C_3F_7$;
  a is zero, 1, 2, 3, 4, 5, 6, 7, 8, 9 or 10;
  m is zero or 1;
  R(13) is hydrogen or alkyl having 1, 2, 3, 4, 5 or 6 carbon atoms;
  or
  R(12) and R(13)
    together are an alkylene group having 4, 5, 6, 7 or 8 carbon atoms,
      where a $CH_2$ group of the alkylene group can be replaced by —O—, —$SO_{zero,\ 1\ or\ 2}$—, —CO— or —NR(11)—;
      R(11) is hydrogen, methyl or ethyl;
R(4) is R(14)—$C_rH_{2r}$;
  r is 1, 2, 3, 4, 5, 6, 7, 8, 9, 10, 11, 12, 13, 14, 15, 16, 17, 18, 19 or 20;
  R(14) is hydrogen, cycloalkyl having 3, 4, 5, 6, 7 or 8 carbon atoms, piperidyl, 1-pyrrolidinyl, N-morpholino, N-methylpiperazino, $CF_3$, $C_2F_5$, $C_3F_7$, pyridyl, thienyl, imidazolyl or phenyl,
    each of which is unsubstituted or substituted by 1 or 2 substituents selected from the group consisting of F, Cl, Br, I, $CF_3$, methyl, methoxy, sulfamoyl, methylsulfonyl and methylsulfonylamino;
  where a $CH_2$ group of the group $C_rH_{2r}$ can be replaced by —O—, —CH=CH—, —C≡C—, —CO—, —CO—O—, —CO—NR(11)—, —$SO_{zero,\ 1\ or\ 2}$— or —NR(11)—;
or
R(3) and R(4)
  together are an alkylene chain having 3, 4, 5, 6, 7 or 8 carbon atoms,
    where a $CH_2$ group of the alkylene chain can be replaced by —O—, —$SO_{zero,\ 1\ or\ 2}$—, —CO— or —NR(11)—;
R(5) and R(6)
  together are —CR(15)=CR(16)—CR(17)=CR(18)—;
  R(15), R(16), R(17) and R(18)
    independently of one another are hydrogen, F, Cl, Br, I, alkyl having 1, 2, 3 or 4 carbon atoms, cycloalkyl having 3, 4, 5, 6, 7 or 8 carbon atoms, CN, $CF_3$, $C_2F_5$, $C_3F_7$, $N_3$, $NO_2$, —CONR(19)R(20), —COOR(21), R(22)—$C_sH_{2s}$—Z— or phenyl,
      each of which is unsubstituted or substituted by 1 or 2 substituents selected from the group consisting of F, Cl, Br, I, $CF_3$, methyl, methoxy, sulfamoyl and methylsulfonyl;
  R(19) and R(20)
    independently of one another are hydrogen or alkyl having 1, 2 or 3 carbon atoms;
  R(21) is hydrogen, methyl, ethyl, phenyl or —$C_uH_{2u}$—NR(19)R(20);
    u is 2 or 3;
      where the phenyl is unsubstituted or substituted by 1 or 2 substituents selected from the group consisting of F, Cl, Br, I, $CF_3$, methyl, methoxy, sulfamoyl or methylsulfonyl;
  R(22) is hydrogen, cycloalkyl having 3, 4, 5, 6, 7 or 8 carbon atoms, —COOR(21), thienyl, imidazolyl, pyridyl, quinolyl, isoquinolyl, piperidyl, 1-pyrrolidinyl, N-morpholino, N-methylpiperazino, $CF_3$, $C_2F_5$ or $C_3F_7$ or phenyl,
    each of which is unsubstituted or substituted by 1 or 2 substituents selected from the group consisting of F, Cl, Br, I, $CF_3$, methyl, methoxy, sulfamoyl or methylsulfonyl;
  s is zero, 1, 2, 3, 4, 5 or 6;
  Z is —$S(O)_{zero,\ 1\ or\ 2}$—, —CO—, —$SO_2$—NR(11)—, —$SO_2$—O—, —O—, —NR(11)— or —CO—NR(11)—;
R(7) is hydrogen, hydroxyl, alkoxy having 1, 2, 3 or 4 carbon atoms, acyloxy having 1, 2, 3 or 4 carbon atoms, Cl, Br, F, alkyl having 1, 2, 3 or 4 carbon atoms;
R(8) is hydrogen or alkyl having 1, 2, 3, 4, 5 or 6 carbon atoms;
and their physiologically tolerable salts.
Very especially preferred compounds of formula I are those in which:
X is —NR(9)— or —CR(9)R(23)—;
  R(9) is hydrogen or —($C_nH_{2n}$)—R(10);
    n is zero, 1, 2, 3 or 4;
    R(10) is hydrogen, cycloalkyl having 3, 4, 5, 6, 7 or 8 carbon atoms, piperidyl, 1-pyrrolidinyl, N-morpholino, N-methylpiperazino, $CF_3$, $C_2F_5$ or $C_3F_7$;
      where a $CH_2$ group of the group $C_nH_{2n}$, can be replaced by —O—, —CH=CH—, —C≡C—, —CO—, —CO—O—, —$SO_{zero,\ 1\ or\ 2}$— or —NR(11)—;
    R(11) is hydrogen, methyl or ethyl;
    or
    R(10) is pyridyl, thienyl, imidazolyl or phenyl, each of which is unsubstituted or substituted by 1 or 2 substituents selected from the group consisting of F, Cl, Br, I, $CF_3$, methyl, methoxy, sulfamoyl, methylsulfonyl and methylsulfonylamino;

R(23) is hydrogen, alkyl having 1, 2 or 3 carbon atoms, OH, O-alkyl having 1, 2 or 3 carbon atoms, COOH, COO-alkyl having 1, 2 or 3 carbon atoms or —CO—R(24);

R(1) and R(2)
independently of one another are hydrogen, $CF_3$, $C_2F_5$, $C_3F_7$, alkyl having 1 or 2 carbon atoms;

or

R(1) and R(2)
together are an alkylene chain having 2, 3, 4, 5 or 6 carbon atoms;

R(3) is R(12)—$C_aH_{2a}$(NR(13))$_m$—;
R(12) is hydrogen or cycloalkyl having 3, 4, 5 or 6 carbon atoms, $CF_3$, $C_2F_5$ or $C_3F_7$;
a is zero, 1, 2, 3, 4, 5 or 6;
m is zero;
R(13) is hydrogen or alkyl having 1, 2, 3, 4, 5 or 6 carbon atoms;

or

R(12) and R(13)
together are an alkylene group having 4, 5, 6, 7 or 8 carbon atoms,
where a $CH_2$ group of the alkylene group can be replaced by —O—, —$SO_{zero,\ 1\ or\ 2}$—, —CO— or —NR(11)—;
R(11) is hydrogen, methyl or ethyl;

R(4) is R(14)—$C_rH_{2r}$;
r is 1, 2, 3, 4, 5, 6, 7, 8, 9 or 10;
R(14) is hydrogen, cycloalkyl having 3, 4, 5, 6, 7 or 8 carbon atoms, piperidyl, 1-pyrrolidinyl, N-morpholino, N-methylpiperazino, $CF_3$, $C_2F_5$, $C_3F_7$, pyridyl, thienyl, imidazolyl or phenyl, each of which is unsubstituted or substituted by 1 or 2 substituents selected from the group consisting of F, Cl, Br, I, $CF_3$, methyl, methoxy, sulfamoyl, methylsulfonyl and methylsulfonylamino;
where a $CH_2$ group of the group $C_rH_{2r}$ can be replaced by —O—, —CH=CH—, —C≡C—, —CO—, —CO—O—, —CO—NR(11)—, —$SO_{zero,\ 1\ or\ 2}$— or —NR(11)—;

or

R(3) and R(4)
together are an alkylene chain having 3, 4, 5, 6, 7 or 8 carbon atoms,
where a $CH_2$ group of the alkylene chain can be replaced by —O—, —$SO_{zero,\ 1\ or\ 2}$—, —CO— or —NR(11)—;

R(5) and R(6)
together are —CR(15)=CR(16)—CR(17)=CR(18)—;
R(15) and R(18)
are hydrogen;
R(16) and R(17)
independently of one another are hydrogen, F, Cl, Br, I, alkyl having 1, 2, 3 or 4 carbon atoms, cycloalkyl having 3, 4, 5, 6, 7 or 8 carbon atoms, CN, $CF_3$, $C_2F_5$, $C_3F_7$, $N_3$, $NO_2$, —CONR(19)R(20), —COOR(21), R(22)—$C_sH_{2s}$—Z— or phenyl,
each of which is unsubstituted or substituted by 1 or 2 substituents selected from the group consisting of F, Cl, Br, I, $CF_3$, methyl, methoxy, sulfamoyl and methylsulfonyl;

R(19) and R(20)
independently of one another are hydrogen or alkyl having 1, 2 or 3 carbon atoms;
R(21) is hydrogen, methyl, ethyl, phenyl or —$C_uH_{2u}$—NR(19)R(20);
u is 2 or 3;
where the phenyl is unsubstituted or substituted by 1 or 2 substituents selected from the group consisting of F, Cl, Br, I, $CF_3$, methyl, methoxy, sulfamoyl or methylsulfonyl;
R(22) is hydrogen, cycloalkyl having 3, 4, 5, 6, 7 or 8 carbon atoms, —COOR(21), thienyl, imidazolyl, pyridyl, quinolyl, isoquinolyl, piperidyl, 1-pyrrolidinyl, N-morpholino, N-methylpiperazino, $CF_3$, $C_2F_5$ or $C_3F_7$ or phenyl,
each of which is unsubstituted or substituted by 1 or 2 substituents selected from the group consisting of F, Cl, Br, I, $CF_3$, methyl, methoxy, sulfamoyl or methylsulfonyl;
s is zero, 1, 2, 3, 4, 5 or 6;
Z is —$S(O)_{zero,\ 1\ or\ 2}$—, —CO—, —$SO_2$—NR(11)—, —$SO_2$—O—, —O—, —NR(11)— or —CO—NR(11)—;
R(7) is hydrogen, hydroxyl, alkoxy having 1, 2, 3 or 4 carbon atoms, acyloxy having 1, 2, 3 or 4 carbon atoms, Cl, Br, F, alkyl having 1, 2, 3 or 4 carbon atoms;
R(8) is hydrogen or alkyl having 1, 2, 3, 4, 5 or 6 carbon atoms;

or pharmaceutically acceptable salts thereof.

If the compounds I contain an acidic or basic group or a basic heterocycle, the invention also relates to the corresponding pharmacologically and toxicologically tolerable salts. Thus the compounds of formula I which carry one or more —COOH groups can be used, for example, as alkali metal salts, preferably as sodium or potassium salts. Compounds of formula I which carry a basic, protonatable group or a basic heterocyclic radical can also be used in the form of their organic or inorganic, pharmacologically and toxicologically tolerable acid addition salts, for example, as hydrochlorides, methanesulfonates, acetates, lactates, maleates, fumarates, malates, gluconates etc. If the compounds of formula I contain an acidic and basic group in the same molecule, beside the salt forms outlined, the invention also includes internal salts, so-called betaines.

If the substituents of compounds of formula I contain groups having different stereochemical possibilities, the invention also includes the individual possible stereoisomers, so that in the case of optical isomerism the individual pure enantiomers and also any desired substance mixtures of these optical isomers are part of the invention.

Alkyl and alkylene radicals can be straight-chain or branched.

The compounds of formula I can be prepared by different chemical processes, which are likewise part of the invention. Thus a compound of the formula I is obtained by a) reacting a compound of formula II

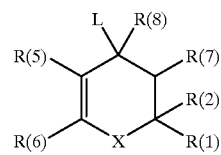

II in which R(1), R(2), R(5), R(6), R(7), R(8) and X have the meaning indicated above and L is a customary nucleofugic leaving group, in particular F, Cl, Br, I, MeSO$_2$—O—, a p-toluenesulfonyloxy radical, or R(7) and L together are an epoxide ring, in a manner known per se with a sulfonamide or its salt of formula III

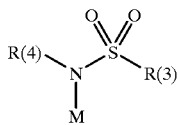

III in which R(3) and R(4) have the meaning indicated above and M is hydrogen or preferably a metal atom, particularly preferably lithium, sodium or potassium;

or by b) reacting a compound of formula IV

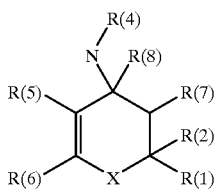

IV in which R(1), R(2), R(4), R(5), R(6), R(7), R(8) and X have the meaning indicated above, with a sulfonic acid derivative of the formula V

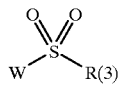

V in which R(3) has the meaning indicated above and W is leaving group, such as fluorine, bromine, 1-imidazolyl, but in particular chlorine;

or by c) reacting a compound of formula VI

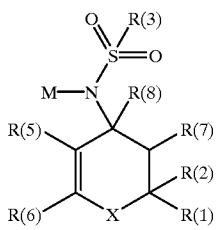

VI in which R(1), R(2), R(3), R(5), R(6), R(7), R(8), X and M have the meaning indicated above, in a manner known per se in the sense of an alkylation reaction, with an alkylating agent of formula VII

R(4)—L    VII in which R(4), with the exception of hydrogen, and L, have the meaning indicated above;

or by d) in a compound of formula I

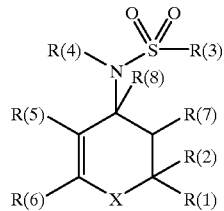

I in which R(1) to R(4), R(7), R(8) and X have the meaning indicated above, carrying out an electrophilic substitution reaction in at least one of the positions R(15), R(16), R(17), R(18) of the ring systems R(5)–R(6) if this position is hydrogen and the remaining substituents R(5) to R(8) have the meaning indicated.

Procedures a through d are first generally described and then utilized in the following examples.

Procedure a) describes the reaction of a sulfonamide or of one of its salts of formula III with a reactive heterocycle of formula II. Since the reaction of a sulfonamide III takes place from the salt form, when using a free sulfonamide (formula III, M=H) a sulfonamide salt (formula III, M=cation) which is distinguished by higher nucleophilicity and thus by higher reactivity must be generated by the action of a base. If free sulfonamide (M=H) is employed, the deprotonation of the sulfonamide to the salt in situ takes place preferably using those bases which themselves are not alkylated or are only slightly alkylated, such as sodium carbonate, potassium carbonate, a sterically strongly hindered amine, e.g. dicyclohexylamine, N,N,N-dicyclohexylethylamine or other strong nitrogen bases having low nucleophilicity, for example DBU, N,N',N'''-triisopropylguanidine etc. However, other customarily used bases can also be employed for the reaction, such as potassium tert-butoxide, sodium methoxide, alkali metal hydrogen carbonates, alkali metal hydroxides, such as, for example, LiOH, NaOH or KOH, or alkali metal hydroxides, for example Ca(OH)$_2$.

The reaction is in this case preferably carried out in polar organic solvents such as dimethylformamide, dimethylacetamide, tetramethylurea, hexamethylphosphoramide, tetrahydrofuran, dimethoxyethane, toluene, a halogenated hydrocarbon such as chloroform or methylene chloride etc. In principle, however, the reaction can also be carried out in polar protic solvents, such as water, methanol, ethanol, isopropanol, ethylene glycol or its oligomers and their corresponding hemiethers and ethers. The reaction is carried out in a preferred temperature range from –10 to 140° C., particularly preferably from 20 to 100° C. Favorably, procedure a) can also be carried out under the conditions of a two-phase catalysis.

The compounds of formula II are obtained by methods known from the literature, for example from the corresponding unsaturated compound shown in formula X:

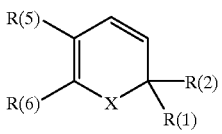

by reaction of an inorganic or organic peroxide, such as, for example, $H_2O_2$, MCPBA, or peracetic acid. The addition of halogen is also possible by the reaction of X with NCS, NBS, chlorine or bromine in aqueous solvents. Advantageously, the reaction is carried out in a solvent which is sufficiently inert to these halogenating or oxidizing reagents, such as, for example, in DMSO or halogenated hydrocarbons such as, for example, chloroform, or methylene chloride.

Procedure b) describes the reaction, which is known per se and frequently used, of a reactive sulfonyl compound of the formula V, in particular of a chlorosulfonyl compound (W=Cl), with an amino derivative of formula IV to give the corresponding sulfonamide derivative of formula I. The reaction can in principle be carried out without solvent, but reactions of this type are in most cases carried out using a solvent.

The reaction preferably takes place using a polar solvent, preferably in the presence of a base which can itself advantageously be used as a solvent, e.g. when using triethylamine, in particular pyridine and its homologs. Solvents also used are, for example, water, aliphatic alcohols, e.g. methanol, ethanol, isopropanol, sec-butanol, ethylene glycol and its monomeric and oligomeric monoalkyl and dialkyl ethers, tetrahydrofuran, dioxane, dialkylated amides such as DMF, DMA, and also TMU and HMPT. The reaction is in this case carried out at a temperature from 0 to 160° C., preferably from 20 to 100° C.

The amino derivatives of formula IV are obtained in a manner known per se from the literature, preferably by reaction of the reactive compounds of formula II where R(1), R(2), R(5), R(6) and L have the meaning indicated, either with ammonia or an amine of the formula XI

R(4)—NH$_2$     XI where R(4) has the meaning indicated.

Procedure c) represents the alkylation reaction, which is known per se, of a sulfonamide or of one of its salts VI with an alkylating agent of formula VII. Corresponding to the reaction analogy with procedure a), the reaction conditions already described in detail under procedure a) apply for procedure c).

The preparation of the sulfonamide derivatives VI and their precursors has already been described in procedure b). The preparation of the alkylating agents VII is carried out according to analogous literature procedures or as described under procedure a), preferably from the corresponding hydroxy compounds (formula VII where L equals —OH).

Procedure d) describes the further chemical conversion of compounds of formula I according to the invention into other compounds of formula I by electrophilic substitution reactions in one or in more of the positions designated by R(5) to R(8), which are each hydrogen.

Preferred Substitution Reactions are:
1. aromatic nitration to introduce one or more nitro groups, and their subsequent reduction to NH$_2$—,
2. aromatic halogenation, in particular to introduce chlorine, bromine or iodine,
3. chlorosulfonation to introduce a chlorosulfonyl group by the action of chlorosulfonic acid,
4. the Friedel-Crafts acylation reaction to introduce an acyl radical R(16)—C$_s$H$_{2s}$—CO— or a sulfonyl radical R(16)—C$_s$H$_{2s}$—SO$_2$— by the action of the corresponding acid chlorides R(16)—C$_s$H$_{2s}$—CO—Cl or R(16)—C$_s$H$_{2s}$—SO$_2$—Cl in the presence of a Lewis acid as a Friedel-Crafts catalyst, preferably of anhydrous aluminum chloride.

The compounds of formula I are related to the class of 4-acylaminochroman derivatives worked on intensively in pharmaceutical chemistry in the last decade, in particular of 2,2-dialkyl-4-acylamino-3-chromanols. The most prominent representative of 4-acylaminochromans of this type is cromakalim (formula XII):

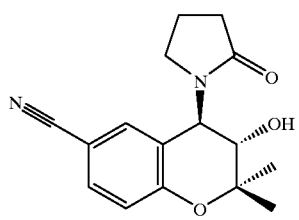

and numerous secondary products deriving from this product (e.g. Edwards and Weston, TIPS 11, 417–422 (1990), "Structure Activity Relationships of K$^+$ Channel Openers").

Cromakalim and other related 4-acylaminochroman derivatives are compounds having a relaxant action on smooth muscular organs, so that they are used for lowering raised blood pressure as a result of vascular muscle relaxation and in the treatment of asthma as a result of relaxation of the smooth musculature of the airways. It is common to all these preparations that they act at the cellular level, for example, of smooth muscle cells and lead there to an opening of certain ATP-sensitive K$^+$ channels. The increase in negative charge in the cell ("hyperpolarization") induced by the efflux of K$^+$ ions counteracts, via secondary mechanisms, the increase in intracellular Ca$^{2+}$ and thus cell activation, e.g. muscle contraction.

In contrast to these 4-acylaminochroman derivatives, which as mentioned have been identified as openers of the ATP-sensitive K$^+$ channel, the compounds of formula I according to the invention with a 4-sulfonylamino structure surprisingly show a strong and specific blocking (closing) action on a K$^+$ channel which is opened by cyclic adenosine monophosphate (cAMP) and differs fundamentally from the K$^+$ (ATP) channel mentioned. More recent investigations on the contrary show that this K$^+$ (cAMP) channel identified in the large intestine is with high probability identical to the I$_{Ks}$ channel identified in the cardiac muscle. As a result of this blocking of the K$^+$(cAMP) channel (=I$_{Ks}$ channel), the compounds display pharmacological actions of high therapeutic utility in the living body.

Thus the compounds are distinguished as a novel active compound class of potent inhibitors of stimulated gastric acid secretion. The compounds of formula I are thus useful medicaments for the treatment of ulcers of the stomach and of the intestinal region, for example of the duodenum. As a result of their strong gastric secretion-inhibiting action, they are likewise suitable as excellent therapeutics for the treatment of reflux esophagitis.

The compounds of the invention are furthermore distinguished by antidiarrheal action and are therefore suitable as pharmaceuticals for the treatment of diarrheal disorders.

The compounds of formula I can furthermore be used as pharmaceuticals for the treatment and prevention of all types of arrhythmias including ventricular and supraventricular arrhythmias. They can be used, in particular, for the control of reentry arrhythmias, atrial fibrillation and for the prevention of sudden heart death as a result of ventricular fibrillation.

Publications now exist in which a correlation between $I_{sK}$ channel-inhibitory action and the suppression of life-threatening cardiac arrhythmias is described, such as are elicited, for example, by β-adrenergic hyperstimulation (e.g. T. J. Colatsky, C. H. Follmer and C. F. Starmer: "Channel Specificity in Antiarrhythmic Drug Action: Mechanism of Potassium Channel Block and its Role in Suppressing and Aggravating Cardiac Arrhythmias", *Circulation* (1990) 82: 2235–2242; A. E. Busch, K. Malloy, W. J. Groh, M. D. Varnum, J. P. Adelman and J. Maylie; "The Novel Class III Antiarrhythmics NE-10064 and NE-10133 Inhibit $I_{sK}$ Channels in Xenopus Oocytes and $I_{Ks}$ in Guinea Pig Cardiac Myocytes", *Biochem. Biophys. Res. Commun.* (1994) 202: 265–270).

2-Carboxy-4-amidotetrahydroquinolones are the subject of a publication (P. D. Leeson et al., *J. Med. Chem.* 35 (1992) 1954–1568, and European Offeniegungsschrift 386 839). The compounds described are both structurally different and not comparable in their pharmacological properties and thus have another therapeutic application area.

Pharmaceuticals which contain a compound of formula I according to the invention can be administered orally, parenterally, intravenously, rectally or by inhalation, the preferred route of administration being dependent on the respective course of the disorder. The inventive compounds of formula I can in this case be used on their own or together with pharmaceutical auxiliaries, namely both in veterinary and in human medicine.

The person skilled in the art is familiar on the basis of his expert knowledge with the auxiliaries which are suitable for the desired pharmaceutical formulation. Beside solvents, gel-forming agents, suppository bases, tablet auxiliaries and other active compound carriers, it is possible to use, for example, antioxidants, dispersants, emulsifiers, antifoams, flavor corrigents, preservatives, solubilizers or colorants.

For an oral use form, the active compounds are mixed with the additives suitable therefor, such as excipients, stabilizers or inert diluents and brought by means of the customary methods into the suitable administration forms, such as tablets, coated tablets, hard capsules, aqueous, alcoholic or oily solutions. Inert carriers which can be used are, for example, gum arabic, magnesia, magnesium carbonate, potassium phosphate, lactose, glucose or starch, in particular corn starch. In this case the preparation can be carried out both as dry and as moist granules. Suitable oily excipients or solvents are, for example, vegetable or animal oils, such as sunflower oil or cod liver oil.

For subcutaneous or intravenous administration, the active compounds, if desired with the substances customary therefor, such as solubilizers, emulsifiers or further auxiliaries, are brought into solution, suspension or emulsion. Possible solvents are, for example: water, physiological saline solution or alcohols, e.g. ethanol, propanol, glycerol, and in addition also sugar solutions such as glucose or mannitol solutions, or alternatively a mixture of the various solvents mentioned.

Suitable pharmaceutical formulations for administration in the form of aerosols or sprays are, for example, solutions, suspensions or emulsions of the active compound of formula I in a pharmaceutically acceptable solvent, such as, in particular, ethanol or water, or a mixture of such solvents. If required, the formulation can also additionally contain other pharmaceutical auxiliaries such as surfactants, emulsifiers and stabilizers as well as a propellant. Such a preparation contains the active compound customarily in a concentration from 0.1 to 10% by weight, in particular from approximately 0.3 to 3% by weight.

The dosage of the active compound of formula I to be administered and the frequency of administration depend on the potency and duration of action of the compounds used; but also on the nature and severity of the illness to be treated and on the sex, age, weight and individual responsiveness of the mammal to be treated.

On average, the daily dose of a compound of formula I in a patient weighing approximately 75 kg is at least 0.001 mg, preferably 0.1 mg, in particular at least 10 g to at most 100 g, preferably at most 1 g per kg.

| Explanation of the abbreviations used in the text | |
|---|---|
| DMA | Dimethylacetamide |
| HMPT | Hexamethylphosphoramide |
| TMU | Tetramethylurea |
| hr | Hour(s) |
| M | Mole |
| MCPBA | m-Chloroperbenzoic acid |
| mmol | Millimole |
| min | Minutes |
| TEA | Triethylamine |
| THF | Tetrahydrofuran |
| NBS | N-Bromosuccinimide |
| NCS | N-Chlorosuccinimide |
| EA | Ethyl acetate |

EXAMPLE 1

N-Methyl-N-(7-nitro-1,2,3,4-tetrahydronaphthalen-1-yl)-methanesulfonamide

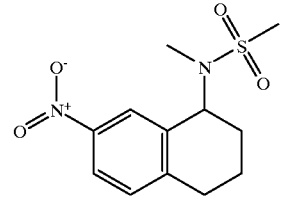

a) 10.0 g (68 mmol) of α-tetralone were dissolved in 80 ml of conc. sulftric acid with ice-cooling. After addition of 6.4 g (75 mmol) of sodium nitrate in portions, the mixture was additionally stirred at 0° C. for 1 h and then poured onto 350 ml of ice water. The precipitated product was filtered off with suction, washed with water until neutral, dried in vacuo and recrystallized from isopropanol. 6.5 g of 7-nitro-3,4-dihydro-2H-naphthalen-1-one were obtained, m.p. 104–106° C.

b) 24 g (314 mmol) of ammonium acetate and 13.8 g (220 mmol) of sodium cyanoborohydride were added to a solution of 6.0 g (31 mmol) of 7-nitro-3,4-dihydro-2H-naphthalen-1-one in 150 ml of methanol, and the reaction mixture was heated at 60° C. for 3 h. After acidifying to pH<2 with dil. hydrochloric acid, the reaction mixture was concentrated in vacuo and the residue was stirred with water and EA. A precipitate which appeared here was filtered off with suction, washed with EA and then combined with the acidic aqueous phase. After rendering the mixture alkaline, it was extracted with EA and the organic phase was dried with magnesium sulfate and concentrated in vacuo. 3.6 g of 7-nitro-1,2,3,4-tetrahydro-1-naphthylamine were obtained.

c) A solution of 2.0 g (10.4 mmol) of 7-nitro-1,2,3,4-tetrahydro-1-naphthylamine in 35 ml of THF was treated with ice-cooling with 4.2 g (41.6 mmol) of triethylamine and 1.3 g (11.4 mmol) of methanesulfonyl chloride and then stirred at RT for 2 hrs. After addition of 20 ml of water, the mixture was concentrated in vacuo down to a 10 ml residue, then treated with a further 20 ml of water, and the precipitated product was filtered off with suction. After drying in vacuo, 2.5 g of N-(7-nitro-1,2,3,4-tetrahydronaphthalen-1-yl)methanesulfonamide were obtained; m.p. 150–152° C.

d) A solution of 1.2 g (4.4 mmol) of N-(7-nitro-1,2,3,4-tetrahydronaphthalen-1-yl)methanesulfonamide in 16 ml of DMF was added dropwise to a suspension of 0.15 g (5.1 nmol) 80 percent sodium hydride in 10 ml of DMF. After stirring at room temperature for 1 hr., 0.62 g (4.4 mmol) of iodomethane were added and the mixture was allowed to stand at room temperature overnight. The reaction mixture was completely concentrated in vacuo and the residue was then taken up in EA and water. After washing the organic phase with dil. hydrochloric acid and sodium bicarbonate solution and concentrating, the residue was purified by chromatography on silica gel using cyclohexane/EA 3:1 and 0.3 g of N-methyl-N-(7-nitro-1,2,3,4-tetrahydronaphthalen-1-yl)methanesulfonamide was obtained; m.p. 138–140° C.

EXAMPLE 2

N-Hexyl-N-(7-nitro-1,2,3,4-tetrahydronaphthalen-1-yl)methanesulfonamide

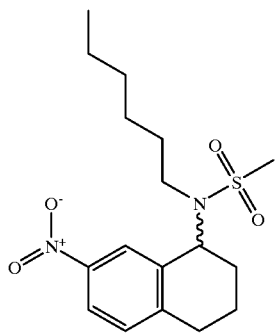

From N-(7-nitro-1,2,3,4-tetrahydronaphthalen-1-yl)methanesulfonamide (Example 1c) and 1-iodohexane, N-hexyl-N-(7-nitro-1,2,3,4-tetrahydronaphthalen-1-yl)methanesulfonamide was obtained analogously to Example 1d as an oil.

EXAMPLE 3

Methyl 5-(methanesulfonyl-methyl-amino)-7,7-dimethyl-5,6,7,8-tetrahydronaphthalene-1-carboxylate

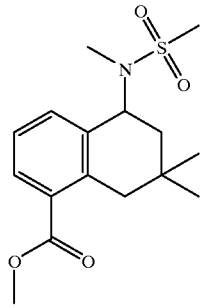

a) A solution of 3.0 g (13 mmol) of methyl 7,7-dimethyl-5-oxo-5,6,7,8-tetrahydro-1-naphthalenecarboxylate (*J. Org. Chem.* 17 (1976), 2918) in 45 ml of methanol was treated with 10 g (130 mmol) of ammonium acetate and 5.7 g (90 mmol) of sodium cyanoborohydride and heated at 60° C. for 20 hrs. After addition of 10 ml of water, the mixture was completely concentrated in vacuo and the residue was taken up in EA and aqueous ammonia. The organic phase was washed with water, dried over magnesium sulfate and concentrated in a rotary evaporator, and 2.9 g of methyl 5-amino-7,7-dimethyl-5,6,7,8-tetrahydro-1-naphthalenecarboxylate were obtained.

b) From 2.8 g of methyl 5-amino-7,7-dimethyl-5,6,7,8-tetrahydro-1-naphthalenecarboxylate, 3.1 g of methyl 5-methanesulfonylamino-7,7-dimethyl-5,6,7,8-tetrahydro-1-naphthalenecarboxylate were obtained analogously to Example 1c; m.p. 136–138° C.

c) A solution of 0.5 g (1.6 mmol) of methyl 5-methanesulfonylamino-7,7-dimethyl-5,6,7,8-tetrahydro-1-naphthalenecarboxylate in 5 ml of DMF was added dropwise to a suspension of 0.05 g (1.8 mmol) of 80 percent sodium hydride in 4 ml of DMF. After stirring at room temperature for 1 hr., 0.23 g (1.6 mmol) of iodomethane was added and the mixture was stirred at room temperature for 4 h. The reaction mixture was completely concentrated in vacuo and the residue was then taken up in EA and water and the organic phase was washed with dilute hydrochloric acid and sodium bicarbonate solution. After drying over magnesium sulfate and concentrating in vacuo; 0.5 g of methyl 5-(methanesulfonyl-methyl-amino)-7,7-dimethyl-5,6,7,8-tetrahydronaphthalene-1-carboxylate was obtained; m.p. 98–99° C.

EXAMPLE 4

Methyl 5-(hexyl-methanesulfonyl-amino)-7,7-dimethyl-5,6,7,8-tetrahydronaphthalene-1-carboxylate

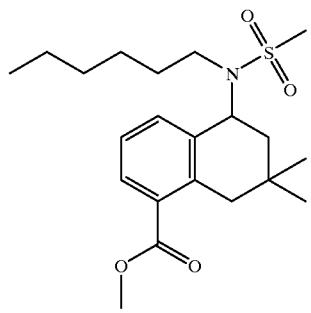

From methyl 5-methanesulfonylamino-7,7-dimethyl-5,6,7,8-tetrahydro-1-naphthalenecarboxylate (Example 3b) and 1-iodohexane, methyl 5-(hexyl-methanesulfonylamino)-7,7-dimethyl-5,6,7,8-tetrahydro-1-naphthalenecarboxylate was obtained analogously to Example 3c as an oil.

EXAMPLE 5

N-(3,3-dimethyl-1,2,3,4-tetrahydronaphthalen-1-yl)-N-methylmethanesulfonamide

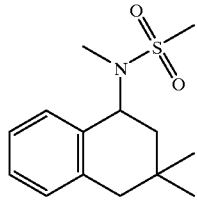

a) A solution of 2.5 g (11 mmol) of methyl 7,7-dimethyl-5-oxo-5,6,7,8-tetrahydro-1-naphthalenecarboxylate (*J. Org. Chem.* 17 (1976), 2918) and 1.8 g (33 mmol) of potassium hydroxide in 50 ml of methanol and 5 ml of water was allowed to stand at room temperature overnight. After distilling off the methanol in vacuo, the residue was taken up in 40 ml of water and the mixture was acidified with dilute hydrochloric acid. The precipitated product was filtered off with suction and dried in vacuo, and 2.3 g of 7,7-dimethyl-5-oxo-5,6,7,8-tetrahydro-1-naphthalenecarboxylic acid were obtained; m.p. 167–168° C.

b) 2.2 g (10 mmol) of 7,7-dimethyl-5-oxo-5,6,7,8-tetrahydro-1-naphthalenecarboxylic acid were heated to 180° C. for 5 h with 2.2 g of copper powder in 22 g of quinoline. After cooling, the mixture was diluted with EA, and the copper was filtered off and then washed several times with dil. hydrochloric acid. After concentration of the organic phase in a rotary evaporator and purification by chromatography on silica gel using cyclohexane/EA 6:1, 0.6 g of 3,3-dimethyl-3,4-dihydro-2H-naphthalen-1-one was obtained.

$^1$H-NMR (200 MHZ, CDCl$_3$): δ (ppm)=1.1 (s, 6H), 2.5 (s, 2H), 2.85 (s, 2H), 7.25 (1H), 7.3 (1H), 7.5 (1H), 8.0 (1H).

c) From 3,3-dimethyl-3,4-dihydro-2H-naphthalen-1-one, N-(3,3-dimethyl-1,2,3,4-tetrahydronaphthalen-1-yl)-N-methylmethanesulfonamide can be obtained analogously to Example 3a–3c.

EXAMPLE 6

N-(3,3-Dimethyl-7-nitro-1,2,3,4-tetrahydronaphthalen-1-yl)-N-methylmethanesulfonamide

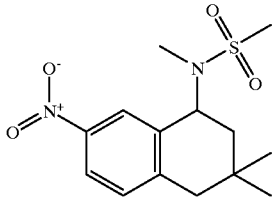

From 3,3-dimethyl-3,4-dihydro-2H-naphthalen-1-one (Example 5b), N-(3,3-dimethyl-7-nitro-1,2,3,4-tetrahydronaphthalen-1-yl)-N-methylmethanesulfonamide can be obtained analogously to Example 1a–1d.

EXAMPLE 7

N-Methyl-N-(1,2,3,4-tetrahydronaphthalen-1-yl)ethanesulfonamide

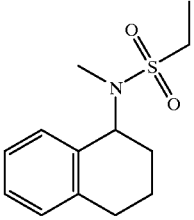

From 1-aminotetralin, N-methyl-N-(1,2,3,4-tetrahydronaphthalen-1-yl)ethanesulfonamide is obtained analogously to Example 1c–1d (from ethanesulfonyl chloride) as an oil.

EXAMPLE 8

N-Butyl-N-(1,2,3,4-tetrahydronaphthalen-1-yl)ethanesulfonamide

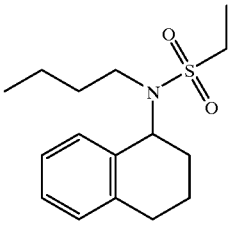

From 1-aminotetralin, N-butyl-N-(1,2,3,4-tetrahydronaphthalen-1-yl)ethanesulfonamide is obtained analogously to Example 1c–1d as an oil.

EXAMPLE 9

N-Methyl-N-(1-phenyl-1,2,3,4-tetrahydroquinolin-4-yl)ethanesulfonamide

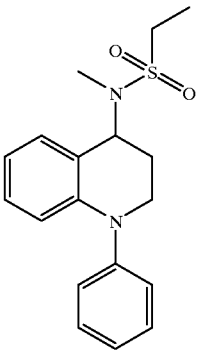

From 1-phenyl-2,3-dihydro-1H-quinolin-4-one, N-methyl-N-(1-phenyl-1,2,3,4-tetrahydroquinolin-4-yl)ethanesulfonamide is obtained analogously to Example 1a–1d as a colorless solid; m.p. 72° C.

EXAMPLE 10

N-Butyl-N-(1-phenyl-1,2,3,4-tetrahydroquinolin-4-yl)ethanesulfonamide

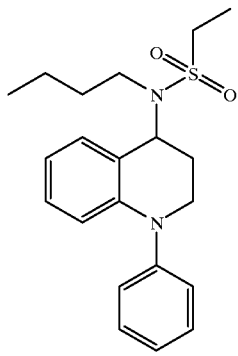

From 1-phenyl-2,3-dihydro-1H-quinolin-4-one, N-butyl-N-(1-phenyl-1,2,3,4-tetrahydroquinolin-4-yl)ethanesulfonamide is obtained analogously to Example 1a–1d as an oil.

What is claimed:
1. A compound of formula I:

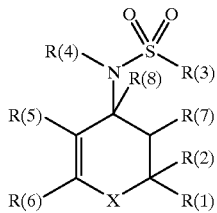

wherein:
X is —CR(9)R(23)— or —CO—;
R(9) is hydrogen or —(C$_n$H$_{2n}$)—R(10);
n is zero, 1, 2, 3, 4, 5, 6, 7, or 8;
R(10) is hydrogen, cycloalkyl having 3, 4, 5, 6, 7, or 8 carbon atoms, piperidyl, 1-pyrrolidinyl, N-morpholino, N-methylpiperazino, CF$_3$, C$_2$F$_5$, or C$_3$F$_7$;
where at least one CH$_2$-group of the group C$_n$H$_{2n}$ is optionally replaced by —O—, —CH=CH—, —C≡C—, —CO—, —CO—O—, —SO$_{zero, 1\, or\, 2}$—, or —NR(11)—;
R(11) is hydrogen, methyl, or ethyl;
or
R(10) is pyridyl, thienyl, imidazolyl or phenyl,
each of which is unsubstituted or substituted by 1 or 2 substituents selected from F, Cl, Br, I, CF$_3$, methyl, methoxy, sulfamoyl, methylsulfonyl, and methylsulfonylamino;
or
R(9) together with R(1) is a bond;
R(23) is hydrogen, alkyl having 1, 2, or 3 carbon atoms, OH, O-alkyl having 1, 2, or 3 carbon atoms, COOH, COO-alkyl having 1, 2, or 3 carbon atoms, or —CO— R(24);
R(24) is hydrogen, methyl, or ethyl;
R(1) and R(2)
each independently represent hydrogen, CF$_3$, C$_2$F$_5$, C$_3$F$_7$, alkyl having 1, 2, 3, 4, 5, or 6 carbon atoms, or phenyl,
each of which is unsubstituted or substituted by 1 or 2 substituents selected from F, Cl, Br, I, CF$_3$, methyl, methoxy, sulfamoyl, and methylsulfonyl;
or
R(1) and R(2)
together are an alkylene chain having 2, 3, 4, 5, 6, 7, 8, 9, or 10 carbon atoms;
R(3) is R(12)—C$_a$H$_{2a}$(NR(13))$_m$—;
R(12) is hydrogen or cycloalkyl having 3, 4, 5, 6, 7, or 8 carbon atoms, CF$_3$, C$_2$F$_5$, or C$_3$F$_7$;
a is zero, 1, 2, 3, 4, 5, 6, 7, 8, 9, or 10;
m is zero or 1;
R(13) is hydrogen or alkyl having 1, 2, 3, 4, 5, or 6 carbon atoms;
or
R(12) and R(13)
together are an alkylene group having 4, 5, 6, 7, or 8 carbon atoms,
where at least one CH$_2$ group of the alkylene group is optionally replaced by —O—, —SO$_{zero, 1\, or\, 2}$—, —CO—, or —NR(11)—;
R(11) is hydrogen, methyl, or ethyl;
R(4) is R(14)—C$_r$H$_{2r}$;
r is 1, 2, 3, 4, 5, 6, 7, 8, 9, 10, 11, 12, 13, 14, 15, 16, 17, 18, 19, or 20;
R(14) is hydrogen, cycloalkyl having 3, 4, 5, 6, 7, or 8 carbon atoms, piperidyl, 1-pyrrolidinyl, N-morpholino, N-methylpiperazino, CF$_3$, C$_2$F$_5$, C$_3$F$_7$, pyridyl, thienyl, imidazolyl, or phenyl,
each of which is unsubstituted or substituted by 1 or 2 substituents selected from F, Cl, Br, I, CF$_3$, methyl, methoxy, sulfamoyl, methylsulfonyl, and methylsulfonylamino;
where at least one CH$_2$ group of the group C$_r$H$_{2r}$ is optionally replaced by —O—, —CH=CH—, —C≡C—, —CO—, —CO—O—, —CO—NR(11)—, —SO$_{zero, 1\, or\, 2}$—, or —NR(11)—;
or
R(3) and R(4)
together are an alkylene chain having 3, 4, 5, 6, 7, or 8 carbon atoms,
where at least one CH$_2$ group of the alkylene chain is optionally replaced by —O—, —SO$_{zero, 1\, or\, 2}$—, —CO—, or —NR(11)—;
R(5) and R(6)
together are —CR(15)=CR(16)—CR(17)=CR(18)—,
R(15), R(16), R(17), and R(18)
each independently represent hydrogen, F, Cl, Br, I, alkyl having 1, 2, 3, or 4 carbon atoms, cycloalkyl having 3, 4, 5, 6, 7, or 8 carbon atoms, CN, CF$_3$, C$_2$F$_5$, C$_3$F$_7$, N$_3$, NO$_2$, —CONR(19)R(20), —COOR(21), R(22)—C$_s$H$_{2s}$—Z—, or phenyl,
each of which is unsubstituted or substituted by 1 or 2 substituents selected from F, Cl, Br, I, CF$_3$, methyl, methoxy, sulfamoyl, and methylsulfonyl;
R(19) and R(20)
each independently represent hydrogen, or alkyl having 1, 2, or 3 carbon atoms;
R(21) is hydrogen, methyl, ethyl, phenyl, or —C$_u$H$_{2u}$—NR(19)R(20);
u is 2, or 3;
where the phenyl is unsubstituted or substituted by 1 or 2 substituents selected from F, Cl, Br, I, CF$_3$, methyl, methoxy, sulfamoyl, and methylsulfonyl;

R(22) is hydrogen, cycloalkyl having 3, 4, 5, 6, 7, or 8 carbon atoms, —COOR(21), thienyl, imidazolyl, pyridyl, quinolyl, isoquinolyl, piperidyl, 1-pyrrolidinyl, N-morpholino, N-methylpiperazino, $CF_3$, $C_2F_5$, $C_3F_7$, or phenyl,
  each of which is unsubstituted or substituted by 1 or 2 substituents selected from F, Cl, Br, I, $CF_3$, methyl, methoxy, sulfamoyl, and methylsulfonyl;
s is zero, 1, 2, 3, 4, 5, or 6;
Z is —S(O)$_{zero, 1\ or\ 2}$—, —CO—, —SO$_2$—NR(11)—, —SO$_2$—O—, —O—, —NR(11)—, or —CO—NR(11)—;
R(7) is hydrogen, hydroxyl, alkoxy having 1, 2, 3, or 4 carbon atoms, acyloxy having 1, 2, 3, or 4 carbon atoms, Cl, Br, F, or alkyl having 1, 2, 3, or 4 carbon atoms;
R(8) is hydrogen or alkyl having 1, 2, 3, 4, 5, or 6 carbon atoms;
or a physiologically tolerable salt thereof.

2. A compound according to claim 1, wherein:
X is —CR(9)R(23)—;
  R(9) is hydrogen or —($C_nH_{2n}$)—R(10);
    n is zero, 1, 2, 3, 4, 5, 6, 7, or 8;
    R(10) is hydrogen, cycloalkyl having 3, 4, 5, 6, 7, or 8 carbon atoms, piperidyl, 1-pyrrolidinyl, N-morpholino, N-methylpiperazino, $CF_3$, $C_2F_5$, or $C_3F_7$;
      where at least one $CH_2$ group of the group $C_nH_{2n}$ is optionally replaced by —O—, —CH=CH—, —C≡C—, —CO—, —CO—O—, —SO$_{zero, 1\ or\ 2}$—, or —NR(11)—;
      R(11) is hydrogen, methyl, or ethyl;
    or
    R(10) is pyridyl, thienyl, imidazolyl, or phenyl,
      each of which is unsubstituted or substituted by 1 or 2 substituents selected from F, Cl, Br, I, $CF_3$, methyl, methoxy, sulfamoyl, methylsulfonyl, and methylsulfonylamino;
  or
  R(9) together with R(1) is a bond;
  R(23) is hydrogen, alkyl having 1, 2, or 3 carbon atoms, OH, O-alkyl having 1, 2, or 3 carbon atoms, COOH, COO-alkyl having 1, 2, or 3 carbon atoms, or —CO—R(24);
  R(24) is hydrogen, methyl, or ethyl,
R(1) and R(2)
  each independently represent hydrogen, $CF_3$, $C_2F_5$, $C_3F_7$, alkyl having 1, 2, 3, 4, 5, or 6 carbon atoms, or phenyl,
    each of which is unsubstituted or substituted by 1 or 2 substituents selected from F, Cl, Br, I, $CF_3$, methyl, methoxy, sulfamoyl, and methylsulfonyl;
or
R(1) and R(2)
  together are an alkylene chain having 2, 3, 4, 5, 6, 7, 8, 9, or 10 carbon atoms;
R(3) is R(12)—$C_aH_{2a}$(NR(13))$_m$—;
  R(12) is hydrogen or cycloalkyl having 3, 4, 5, 6, 7, or 8 carbon atoms, $CF_3$, $C_2F_5$, or $C_3F_7$;
  a is zero, 1, 2, 3, 4, 5, 6, 7, 8, 9, or 10;
  m is zero or 1;
  R(13) is hydrogen or alkyl having 1, 2, 3, 4, 5, or 6 carbon atoms;
  or
  R(12) and R(13)
    together are an alkylene group having 4, 5, 6, 7, or 8 carbon atoms,
    where at least one $CH_2$ group of the alkylene group is optionally replaced by —O—, —SO$_{zero, 1\ or\ 2}$—, —CO— or —NR(11)—;
  R(11) is hydrogen, methyl, or ethyl;
R(4) is R(14)—$C_rH_{2r}$;
  r is 1, 2, 3, 4, 5, 6, 7, 8, 9, 10, 11, 12, 13, 14, 15, 16, 17, 18, 19, or 20;
  R(14) is hydrogen, cycloalkyl having 3, 4, 5, 6, 7, or 8 carbon atoms, piperidyl, 1-pyrrolidinyl, N-morpholino, N-methylpiperazino, $CF_3$, $C_2F_5$, $C_3F_7$, pyridyl, thienyl, imidazolyl or phenyl,
    each of which is unsubstituted or substituted by 1 or 2 substituents selected from F, Cl, Br, I, $CF_3$, methyl, methoxy, sulfamoyl, methylsulfonyl, and methylsulfonylamino;
  where at least one $CH_2$ group of the group $C_rH_{2r}$ is optionally replaced by —O—, —CH=CH—, —C≡C—, —CO—, —CO—O—, —CO—NR(11)—, —SO$_{zero, 1\ or\ 2}$—, or —NR(11)—;
or
R(3) and R(4)
  together are an alkylene chain having 3, 4, 5, 6, 7, or 8 carbon atoms,
    where at least one $CH_2$ group of the alkylene chain can be replaced by —O—, —SO$_{zero, 1\ or\ 2}$—, —CO—, or —NR(11)—;
R(5) and R(6)
  together are —CR(15)=CR(16)—CR(17)=CR(18)—;
  R(15), R(16), R(17), and R(18)
    each independently represent hydrogen, F, Cl, Br, I, alkyl having 1, 2, 3, or 4 carbon atoms, cycloalkyl having 3, 4, 5, 6, 7, or 8 carbon atoms, CN, $CF_3$, $C_2F_5$, $C_3F_7$, $N_3$, $NO_2$, —CONR(19)R(20), —COOR(21), R(22)—$C_sH_{2s}$—Z—, or phenyl,
      each of which is unsubstituted or substituted by 1 or 2 substituents selected from F, Cl, Br, I, $CF_3$, methyl, methoxy, sulfamoyl, and methylsulfonyl,
  R(19) and R(20)
    independently of one another are hydrogen or alkyl having 1, 2, or 3 carbon atoms;
  R(21) is hydrogen, methyl, ethyl, phenyl or —$C_uH_{2u}$—NR(19)R(20);
  u is 2 or 3;
    where the phenyl is unsubstituted or substituted by 1 or 2 substituents selected from F, Cl, Br, I, $CF_3$, methyl, methoxy, sulfamoyl, and methylsulfonyl;
  R(22) is hydrogen, cycloalkyl having 3, 4, 5, 6, 7, or 8 carbon atoms, —COOR(21), thienyl, imidazolyl, pyridyl, quinolyl, isoquinolyl, piperidyl, 1-pyrrolidinyl, N-morpholino, N-methylpiperazino, $CF_3$, $C_2F_5$, $C_3F_7$, or phenyl,
    each of which is unsubstituted or substituted by 1 or 2 substituents selected from F, Cl, Br, I, $CF_3$, methyl, methoxy, sulfamoyl, and methylsulfonyl;
  s is zero, 1, 2, 3, 4, 5, or 6;
  Z is —S(O)$_{zero, 1\ or\ 2}$—, —CO—, SO$_2$—NR(11)—, —SO$_2$—O—, —O—, —NR(11)—, or —CO—NR(11)—;
R(7) is hydrogen, hydroxyl, alkoxy having 1, 2, 3, or 4 carbon atoms, acyloxy having 1, 2, 3, or 4 carbon atoms, Cl, Br, F, or alkyl having 1, 2, 3, or 4 carbon atoms; and
R(8) is hydrogen or alkyl having 1, 2, 3, 4, 5, or 6 carbon atoms; or a physiologically tolerable salt thereof.

3. The compound according to claim 1, wherein:
X is —CR(9)R(23)—;
   R(9) is hydrogen or —$(C_nH_{2n})$—R(10);
      n is zero, 1, 2, 3, 4, 5, 6, 7, or 8;
      R(10) is hydrogen, cycloalkyl having 3, 4, 5, 6, 7, or 8 carbon atoms, piperidyl, 1-pyrrolidinyl, N-morpholino, N-methylpiperazino, $CF_3$, $C_2F_5$, or $C_3F_7$;
      where a $CH_2$ group of the group $C_nH_{2n}$ can be replaced by —O—, —CH=CH—, —C≡C—, —CO—, —CO—O—, —$SO_{zero,\ 1\ or\ 2}$—, or —NR(11)—;
         R(11) is hydrogen, methyl or ethyl;
   or
      R(10) is pyridyl, thienyl, imidazolyl, or phenyl,
         each of which is unsubstituted or substituted by 1 or 2 substituents selected from F, Cl, Br, I, $CF_3$, methyl, methoxy, sulfamoyl, methylsulfonyl, and methylsulfonylamino;
or
   R(9) together with R(1) is a bond;
   R(23) is hydrogen, alkyl having 1, 2, or 3 carbon atoms, OH, O-alkyl having 1, 2, or 3 carbon atoms, COOH, COO-alkyl having 1, 2, or 3 carbon atoms, or —CO—R(24);
   R(24) is hydrogen, methyl, or ethyl;
R(1) and R(2)
   each independently represent hydrogen, $CF_3$, $C_2F_5$, $C_3F_7$, alkyl having 1, 2, 3, 4, 5, or 6 carbon atoms, or phenyl,
      each of which is unsubstituted or substituted by 1 or 2 substituents selected from F, Cl, Br, I, $CF_3$, methyl, methoxy, sulfamoyl, and methylsulfonyl;
or
R(1) and R(2)
   together are an alkylene chain having 2, 3, 4, 5, 6, 7, 8, 9, or 10 carbon atoms; R(3) is R(12)—$C_aH_{2a}$(NR(13))$_m$—;
   R(12) is hydrogen, cycloalkyl having 3, 4, 5, 6, 7, or 8 carbon atoms, $CF_3$, $C_2F_5$, or $C_3F_7$;
   a is zero, 1, 2, 3, 4, 5, 6, 7, 8, 9, or 10;
   m is zero or 1;
   R(13) is hydrogen or alkyl having 1, 2, 3, 4, 5, or 6 carbon atoms;
   or
   R(12) and R(13)
      together are an alkylene group having 4, 5, 6, 7, or 8 carbon atoms,
         where at least one $CH_2$ group of the alkylene group is optionally replaced by —O—, —$SO_{zero,\ 1\ or\ 2}$—, —CO—, or —NR(11)—;
         R(11) is hydrogen, methyl, or ethyl;
R(4) is R(14)—$C_rH_{2r}$;
   r is 1, 2, 3, 4, 5, 6, 7, 8, 9, or 10;
   R(14) is cycloalkyl having 3, 4, 5, 6, 7, or 8 carbon atoms, piperidyl, 1-pyrrolidinyl, N-morpholino, N-methylpiperazino, $CF_3$, $C_2F_5$, $C_3F_7$, pyridyl, thienyl, imidazolyl, or phenyl,
      each of which is unsubstituted or substituted by 1 or 2 substituents selected from F, Cl, Br, I, $CF_3$, methyl, methoxy, sulfamoyl, methylsulfonyl, and methylsulfonylamino;
   where at least one $CH_2$ group of the group $C_rH_{2r}$ is optionally replaced by —O—, —CH=CH—, —C≡C—, —CO—, —CO—O—, —CO—NR(11)—, —$SO_{zero,\ 1\ or\ 2}$—, or —NR(11)—;
or
R(3) and R(4)
   together are an alkylene chain having 3, 4, 5, 6, 7, or 8 carbon atoms,
      where at least one $CH_2$ group of the alkylene chain is optionally replaced by —O—, —$SO_{zero,\ 1\ or\ 2}$—, —CO—, or —NR(11)—;
R(5) and R(6)
   together are —CR(15)=CR(16)—CR(17)=CR(18)—;
   R(15), R(16), R(17), and R(18)
      independently of one another are hydrogen, F, Cl, Br, I, alkyl having 1, 2, 3, or 4 carbon atoms, cycloalkyl having 3, 4, 5, 6, 7, or 8 carbon atoms, CN, $CF_3$, $C_2F_5$, $C_3F_7$, $N_3$, $NO_2$, —CONR(19)R(20), —COOR(21), R(22)—$C_sH_{2s}$—Z—, or phenyl,
         each of which is unsubstituted or substituted by 1 or 2 substituents selected from F, Cl, Br, I, $CF_3$, methyl, methoxy, sulfamoyl, and methylsulfonyl;
   R(19) and R(20)
      each independently represent hydrogen or alkyl having 1, 2, or 3 carbon atoms;
   R(21) is hydrogen, methyl, ethyl, phenyl, or —$C_uH_{2u}$—NR(19)R(20);
   u is 2 or 3;
      where the phenyl is unsubstituted or substituted by 1 or 2 substituents selected from F, Cl, Br, I, $CF_3$, methyl, methoxy, sulfamoyl, and methylsulfonyl;
   R(22) is hydrogen, cycloalkyl having 3, 4, 5, 6, 7, or 8 carbon atoms, —COOR(21), thienyl, imidazolyl, pyridyl, quinolyl, isoquinolyl, piperidyl, 1-pyrrolidinyl, N-morpholino, N-methylpiperazino, $CF_3$, $C_2F_5$, $C_3F_7$, or phenyl,
      each of which is unsubstituted or substituted by 1 or 2 substituents selected from F, Cl, Br, I, $CF_3$, methyl, methoxy, sulfamoyl, and methylsulfonyl;
   s is zero, 1, 2, 3, 4, 5, or 6;
   Z is —$S(O)_{zero,\ 1\ or\ 2}$—, —CO—, —$SO_2$—NR(11)—, —$SO_2$—O—, —O—, —NR(11)—, or —CO—NR(11)—,
R(7) is hydrogen, hydroxyl, alkoxy having 1, 2, 3, or 4 carbon atoms, acyloxy having 1, 2, 3, or 4 carbon atoms, Cl, Br, F, or alkyl having 1, 2, 3, or 4 carbon atoms;
R(8) is hydrogen or alkyl having 1, 2, 3, 4, 5, or 6 carbon atoms;
or a physiologically tolerable salt thereof.

4. A compound according to claim 1, wherein:
X is —CR(9)R(23)—;
   R(9) is hydrogen or —$(C_nH_{2n})$—R(10);
      n is zero, 1, 2, 3, 4, 5, 6, 7, or 8;
      R(10) is hydrogen, cycloalkyl having 3, 4, 5, 6, 7, or 8 carbon atoms, piperidyl, 1-pyrrolidinyl, N-morpholino, N-methylpiperazino, $CF_3$, $C_2F_5$, or $C_3F_7$;
      where at least one $CH_2$ group of the group $C_nH_{2n}$ is optionally replaced by —O—, —CH=CH—, —C≡C—, —CO—, —CO—O—, —$SO_{zero,\ 1\ or\ 2}$—, or —NR(11)—;
         R(11) is hydrogen, methyl or ethyl;
   or
      R(10) is pyridyl, thienyl, imidazolyl or phenyl,
         each of which is unsubstituted or substituted by 1 or 2 substituents selected from F, Cl, Br, I, $CF_3$, methyl, methoxy, sulfamoyl, methylsulfonyl, and methylsulfonylamino;

R(23) is hydrogen, alkyl having 1, 2, or 3 carbon atoms, OH, O-alkyl having 1, 2, or 3 carbon atoms, COOH, COO-alkyl having 1, 2, or 3 carbon atoms, or —CO—R(24);

R(1) and R(2)
each independently represent hydrogen, $CF_3$, $C_2F_5$, $C_3F_7$, alkyl having 1, 2, 3, 4, 5, or 6 carbon atoms, or phenyl,
each of which is unsubstituted or substituted by 1 or 2 substituents selected from F, Cl, Br, I, $CF_3$, methyl, methoxy, sulfamoyl, and methylsulfonyl;

or

R(1) and R(2)
together are an alkylene chain having 2, 3, 4, 5, 6, 7, 8, 9, or 10 carbon atoms;

R(3) is R(12)—$C_aH_{2a}$(NR(13))$_m$—;
R(12) is hydrogen, cycloalkyl having 3, 4, 5, 6, 7, or 8 carbon atoms, $CF_3$, $C_2F_5$, or $C_3F_7$;
a is zero, 1, 2, 3, 4, 5, 6, 7, 8, 9, or 10;
m is zero or 1;
R(13) is hydrogen or alkyl having 1, 2, 3, 4, 5, or 6 carbon atoms;

or

R(12) and R(13)
together are an alkylene group having 4, 5, 6, 7, or 8 carbon atoms,
where at least one $CH_2$ group of the alkylene group is optionally replaced by —O—, —SO$_{zero, 1\ or\ 2}$—, —CO—, or —NR(11)—;
R(11) is hydrogen, methyl, or ethyl;

R(4) is R(14)—$C_rH_{2r}$;
r is 1, 2, 3, 4, 5, 6, 7, 8, 9, 10, 11, 12, 13, 14, 15, 16, 17, 18, 19, or 20;
R(14) is hydrogen, cycloalkyl having 3, 4, 5, 6, 7, or 8 carbon atoms, piperidyl, 1-pyrrolidinyl, N-morpholino, N-methylpiperazino, $CF_3$, $C_2F_5$, $C_3F_7$, pyridyl, thienyl, imidazolyl, or phenyl,
each of which is unsubstituted or substituted by 1 or 2 substituents selected from F, Cl, Br, I, $CF_3$, methyl, methoxy, sulfamoyl, methylsulfonyl, and methylsulfonylamino;
where a $CH_2$ group of the group $C_rH_{2r}$ can be replaced by —O—, —CH=CH—, —C≡C—, —CO—, —CO—O—, —CO—NR(11)—, —SO$_{zero, 1\ or\ 2}$—, or —NR(11)—, or R(3) and R(4)
together are an alkylene chain having 3, 4, 5, 6, 7, or 8 carbon atoms,
where at least one $CH_2$ group of the alkylene chain is optionally replaced by —O—, —SO$_{zero, 1\ or\ 2}$—, —CO—, or —NR(11)—;

R(5) and R(6)
together are —CR(15)=CR(16)—CR(17)=CR(18)—;
R(15), R(16), R(17), and R(18)
each independently represent hydrogen, F, Cl, Br, I, alkyl having 1, 2, 3, or 4 carbon atoms, cycloalkyl having 3, 4, 5, 6, 7, or 8 carbon atoms, CN, $CF_3$, $C_2F_5$, $C_3F_7$, $N_3$, $NO_2$, —CONR(19)R(20), —COOR(21), R(22)—$C_sH_{2s}$—Z—, or phenyl,
each of which is unsubstituted or substituted by 1 or 2 substituents selected from F, Cl, Br, I, $CF_3$, methyl, methoxy, sulfamoyl, and methylsulfonyl;

R(19) and R(20)
each independently represent hydrogen or alkyl having 1, 2, or 3 carbon atoms;
R(21) is hydrogen, methyl, ethyl, phenyl or —$C_uH_{2u}$—NR(19)R(20);
u is 2 or 3;
where the phenyl is unsubstituted or substituted by 1 or 2 substituents selected from F, Cl, Br, I, $CF_3$, methyl, methoxy, sulfamoyl, and methylsulfonyl;
R(22) is hydrogen, cycloalkyl having 3, 4, 5, 6, 7, or 8 carbon atoms, —COOR(21), thienyl, imidazolyl, pyridyl, quinolyl, isoquinolyl, piperidyl, 1-pyrrolidinyl, N-morpholino, N-methylpiperazino, $CF_3$, $C_2F_5$, $C_3F_7$, or phenyl,
each of which is unsubstituted or substituted by 1 or 2 substituents selected from F, Cl, Br, I, $CF_3$, methyl, methoxy, sulfamoyl, and methylsulfonyl;
s is zero, 1, 2, 3, 4, 5, or 6;
Z is —S(O)$_{zero, 1\ or\ 2}$—, —CO—, —SO$_2$—NR(11)—, —SO$_2$—O—, —O—, —NR(11)—, or —CO—NR(11)—;

R(7) is hydrogen, hydroxyl, alkoxy having 1, 2, 3, or 4 carbon atoms, acyloxy having 1, 2, 3, or 4 carbon atoms, Cl, Br, F, or alkyl having 1, 2, 3, or 4 carbon atoms;

R(8) is hydrogen or alkyl having 1, 2, 3, 4, 5, or 6 carbon atoms;

or a physiologically tolerable salt thereof.

5. A compound according to claim 1, wherein:
X is —CR(9)R(23)—;
R(9) is hydrogen or —($C_nH_{2n}$)—R(10);
n is zero, 1, 2, 3, or 4;
R(10) is hydrogen, cycloalkyl having 3, 4, 5, 6, 7, or 8 carbon atoms, piperidyl, 1-pyrrolidinyl, N-morpholino, N-methylpiperazino, $CF_3$, $C_2F_5$, or $C_3F_7$;
where at least one $CH_2$ group of the group $C_nH_{2n}$ is optionally replaced by —O—, —CH=CH—, —C≡C—, —CO—, —CO—O—, —SO$_{zero, 1\ or\ 2}$—, or —NR(11)—;
R(11) is hydrogen, methyl, or ethyl;

or

R(10) is pyridyl, thienyl, imidazolyl, or phenyl,
each of which is unsubstituted or substituted by 1 or 2 substituents selected from F, Cl, Br, I, $CF_3$, methyl, methoxy, sulfamoyl, methylsulfonyl, and methylsulfonylamino;

R(23) is hydrogen, alkyl having 1, 2, or 3 carbon atoms, OH, O-alkyl having 1, 2, or 3 carbon atoms, COOH, COO-alkyl having 1, 2, or 3 carbon atoms, or —CO—R(24);

R(1) and R(2)
each independently represent hydrogen, $CF_3$, $C_2F_5$, $C_3F_7$, or alkyl having 1 or 2 carbon atoms;

or

R(1) and R(2)
together are an alkylene chain having 2, 3, 4, 5, or 6 carbon atoms;

R(3) is R(12)—$C_aH_{2a}$(NR(13))$_m$—;
R(12) is hydrogen or cycloalkyl having 3, 4, 5, or 6 carbon atoms, $CF_3$, $C_2F_5$, or $C_3F_7$;
a is zero, 1, 2, 3, 4, 5, or 6;
m is zero;
R(13) is hydrogen or alkyl having 1, 2, 3, 4, 5, or 6 carbon atoms;

or

R(12) and R(13)
together are an alkylene group having 4, 5, 6, 7, or 8 carbon atoms,
where at least one $CH_2$ group of the alkylene group is optionally replaced by —O—, —$SO_{zero, 1\ or\ 2}$—, —CO—, or —NR(11)—;
R(11) is hydrogen, methyl, or ethyl;

R(4) is R(14)—$C_rH_{2r}$—;

r is 1, 2, 3, 4, 5, 6, 7, 8, 9, or 10;

R(14) is hydrogen, cycloalkyl having 3, 4, 5, 6, 7, or 8 carbon atoms, piperidyl, 1-pyrrolidinyl, N-morpholino, N-methylpiperazino, $CF_3$, $C_2F_5$, $C_3F_7$, pyridyl, thienyl, imidazolyl, or phenyl,
each of which is unsubstituted or substituted by 1 or 2 substituents selected from F, Cl, Br, I, $CF_3$, methyl, methoxy, sulfamoyl, methylsulfonyl, and methylsulfonylamino;

where at least one $CH_2$ group of the group $C_rH_{2r}$ is optionally replaced by —O—, —CH=CH—, —C≡C—, —CO—, —CO—O—, —CO—NR(11)—, —$SO_{zero, 1\ or\ 2}$—, or —NR(11)—;

or

R(3) and R(4)
together are an alkylene chain having 3, 4, 5, 6, 7, or 8 carbon atoms,
where at least one $CH_2$ group of the alkylene chain is optionally replaced by —O—, —$SO_{zero, 1\ or\ 2}$—, —CO—, or —NR(11)—;

R(5) and R(6)
together are —CR(15)=CR(16)—CR(17)=CR(18)—;

R(15) and R(18)
are hydrogen,

R(16) and R(17)
each independently represent hydrogen, F, Cl, Br, I, alkyl having 1, 2, 3, or 4 carbon atoms, cycloalkyl having 3, 4, 5, 6, 7, or 8 carbon atoms, CN, $CF_3$, $C_2F_5$, $C_3F_7$, $N_3$, $NO_2$, —CONR(19)R(20), —COOR(21), R(22)—$C_sH_{2s}$—Z—, or phenyl,
each of which is unsubstituted or substituted by 1 or 2 substituents selected from F, Cl, Br, I, $CF_3$, methyl, methoxy, sulfamoyl, and methylsulfonyl;

R(19) and R(20)
each independently represent hydrogen or alkyl having 1, 2, or 3 carbon atoms;

R(21) is hydrogen, methyl, ethyl, phenyl, or —$C_uH_{2u}$—NR(19)R(20);

u is 2 or 3;
where the phenyl is unsubstituted or substituted by 1 or 2 substituents selected from F, Cl, Br, I, $CF_3$, methyl, methoxy, sulfamoyl, and methylsulfonyl;

R(22) is hydrogen, cycloalkyl having 3, 4, 5, 6, 7, or 8 carbon atoms, —COOR(21), thienyl, imidazolyl, pyridyl, quinolyl, isoquinolyl, piperidyl, 1-pyrrolidinyl, N-morpholino, N-methylpiperazino, $CF_3$, $C_2F_5$, $C_3F_7$, or phenyl,
each of which is unsubstituted or substituted by 1 or 2 substituents selected from F, Cl, Br, I, $CF_3$, methyl, methoxy, sulfamoyl, and methylsulfonyl;

s is zero, 1, 2, 3, 4, 5, or 6;

Z is —$S(O)_{zero, 1\ or\ 2}$—, —CO—, —$SO_2$—NR(11)—, —$SO_2$—O—, —O—, —NR(11)—, or —CO—NR(11)—;

R(7) is hydrogen, hydroxyl, alkoxy having 1, 2, 3, or 4 carbon atoms, acyloxy having 1, 2, 3, or 4 carbon atoms, Cl, Br, F, or alkyl having 1, 2, 3, or 4 carbon atoms; and R(8) is hydrogen or alkyl having 1, 2, 3, 4, 5, or 6 carbon atoms;

or a physiologically tolerable salt thereof.

6. A method for treating or preventing illnesses in which a cAMP opened $K^+$ channel is implicated, comprising administering to a host in need thereof an amount of a compound according to claim 1 or a physiologically tolerable salt thereof effective to block opening of the $K^+$ channel.

7. A method for treating or preventing cardiac arrhythmias, comprising administering to a host in need thereof an effective amount of a compound according to claim 1 or a physiologically tolerable salt thereof.

8. A method for treating or preventing atrial fibrillation or atrial flutter comprising administering to a host in need thereof an effective amount of a compound according to claim 1 or a physiologically tolerable salt thereof.

9. A method for treating or preventing stimulated gastric acid secretion, comprising administering to a host in need thereof an effective amount of a compound according to claim 1 or a physiologically tolerable salt thereof.

10. A method for treating or preventing ulcers of the stomach and of the intestinal region, comprising administering to a host in need thereof an effective amount of a compound according to claim 1 or a physiologically tolerable salt thereof.

11. A method for treating or preventing reflux esophagitis, comprising administering to a host in need thereof an effective amount of a compound of claim 1 or a physiologically tolerable salt thereof.

12. A method for treating or preventing diarrhea, comprising administering to a host in need thereof an effective amount of a compound of claim 1 or a physiologically tolerable salt thereof.

13. A method for treating or preventing arrhythmias, comprising administering to a host in need thereof an effective amount of a compound of claim 1 or a physiologically tolerable salt thereof.

14. A method according to claim 13, wherein said arrhythmias are ventricular or supraventricular.

15. A method for treating or preventing reentry arrhythmias, comprising administering to a host in need thereof an effective amount of a compound of claim 1 or a physiologically tolerable salt thereof.

16. A method for treating or preventing sudden heart death as a result of ventricular fibrillation, comprising administering to a host in need thereof an effective amount of a compound of claim 1 or a physiologically tolerable salt thereof.

17. A pharmaceutical composition, comprising a compound according to claim 1 or a physiologically tolerable salt thereof and a pharmaceutically acceptable carrier.

* * * * *